US009320586B2

(12) United States Patent
Amarasinghe et al.

(10) Patent No.: US 9,320,586 B2
(45) Date of Patent: Apr. 26, 2016

(54) SURGICAL IMPLANT FOR TREATING PELVIC ORGAN PROLAPSE CONDITIONS

(75) Inventors: Chanaka Amarasinghe, Monmouth Junction, NJ (US); Marc E. Feinberg, Ringoes, NJ (US)

(73) Assignee: Ethicon, Inc., Somerville, NJ (US)

( * ) Notice: Subject to any disclaimer, the term of this patent is extended or adjusted under 35 U.S.C. 154(b) by 167 days.

(21) Appl. No.: 13/539,934

(22) Filed: Jul. 2, 2012

(65) Prior Publication Data

US 2014/0005471 A1 Jan. 2, 2014

(51) Int. Cl.
*A61F 2/00* (2006.01)
*A61F 13/00* (2006.01)

(52) U.S. Cl.
CPC ............. *A61F 2/0004* (2013.01); *A61F 2/0045* (2013.01); *A61F 2/0095* (2013.01); *A61F 2250/0018* (2013.01); *A61F 2250/0085* (2013.01)

(58) Field of Classification Search
CPC ................ A61F 2/0004; A61F 2/0045; A61F 2250/0085; A61F 2/0095; A61F 2250/0018; A61F 2017/00805
USPC ......................... 600/29, 30, 37; 128/834, 885
See application file for complete search history.

(56) References Cited

U.S. PATENT DOCUMENTS 4,769,038 A 9/1988 Bendavid et al.
6,575,897 B1 * 6/2003 Ory et al. ........................ 600/30
6,592,515 B2 7/2003 Thierfelder et al.
6,884,212 B2 4/2005 Thierfelder et al.
7,025,063 B2 4/2006 Snitkin et al.
7,517,313 B2 4/2009 Thierfelder et al.
7,740,576 B2 * 6/2010 Hodroff et al. ................. 600/29
7,811,223 B2 10/2010 Hodroff et al.
2002/0028980 A1 * 3/2002 Thierfelder et al. ............ 600/37

(Continued)

FOREIGN PATENT DOCUMENTS

WO WO 2009/017680 A2 2/2009
WO WO 2009/017680 A3 2/2009

(Continued)

OTHER PUBLICATIONS

Alyte Y-Mesh Graft, a lightweight solution optimized for procedural efficiency. Bard Medical Division Brochure, C.R. Bard, Inc., 8195 Industrial Blvd., Covington, GA 30014, USA, www.bardmedical.com 2011.

(Continued)

*Primary Examiner* — Navin Natnithithadha
*Assistant Examiner* — Sunita Reddy
(74) *Attorney, Agent, or Firm* — Melissa J. Szanto

(57) ABSTRACT

An implant including a vaginal portion having a length, width, first and second ends with a central region positioned therebetween, and a sacral portion having a length, width, first end and second end. The first end of the sacral portion is coupled to the central region of the vaginal portion so that the width of the first end extends substantially perpendicularly to the length of the vaginal portion. The implant is made of the same substantially flat, planar mesh having an anisotropic knitted or woven structure that has a greater stiffness in a first direction than a second direction. The mesh is aligned such that the first direction is aligned in a longitudinal direction of the sacral portion and the mesh of the vaginal portion is aligned such that the stiffness in a longitudinal direction of the vaginal portion is less than that of the sacral portion.

7 Claims, 5 Drawing Sheets

105
103
104

(56) References Cited

U.S. PATENT DOCUMENTS

| | | | | |
|---|---|---|---|---|
| 2003/0216814 | A1 | 11/2003 | Siegel et al. | |
| 2004/0054253 | A1 | 3/2004 | Snitkin et al. | |
| 2004/0225181 | A1* | 11/2004 | Chu et al. | 600/37 |
| 2007/0293717 | A1 | 12/2007 | Kaleta et al. | |
| 2008/0021265 | A1* | 1/2008 | Garbin et al. | 600/30 |
| 2008/0132754 | A1 | 6/2008 | Thierfelder et al. | |
| 2009/0163936 | A1* | 6/2009 | Yang et al. | 606/151 |
| 2011/0297161 | A1* | 12/2011 | Deitch | 128/834 |
| 2012/0108894 | A1* | 5/2012 | Young et al. | 600/37 |
| 2013/0204077 | A1* | 8/2013 | Nagale et al. | 600/37 |
| 2013/0317286 | A1* | 11/2013 | Bluecher et al. | 600/37 |

FOREIGN PATENT DOCUMENTS

| | | | |
|---|---|---|---|
| WO | WO 2009/017680 | A4 | 2/2009 |
| WO | WO 2010/087923 | A1 | 8/2010 |
| WO | WO 2012/054985 | A1 | 5/2012 |

OTHER PUBLICATIONS

Alyte® y-Mesh Graft, Bard Medical Brochure, Copyright © 2012 C.R. Bard, Inc.

Alyte® Y-Mesh Graft, The new solution for solution for sacrocolposuspension/sacrocolpopexy procedures. C.R. Bard, Inc., Covington, GA 30014, www.bardmedical.com, © 2011 C.R. Bard, Inc.

AMS Medical Solutions, "Straight-In™" Overview, AMS an endo health solution, www.americanmedicalsystems.com/prof_detail_objectname_prof_fe_male_straightin.html (as of Jul. 27, 2012).

Bard: Pelvic Organ Prolapse "An overview of Pelvic Organ Prolapse" Brochure, C.R. Bard, Inc. Covington, GA 30014, www.bardmedical.com © 2011 C.R. Bard, Inc.

Restorelle™y, Smartmesh™ Technology, Mpathy Medical, www.mpathymedical.com/foundations/store/storepage.asp?page=RestY (Nov. 15, 2011).

International Search Report dated Sep. 5, 2013 for PCT/US2013/048613 filed Jun. 28, 2013.

* cited by examiner 300
302
303
304
305
306
308
309
310
311
312
314
315
316
317
318
320
321
322
323
324
330
331
332
333
334
A
A FIG. 4a
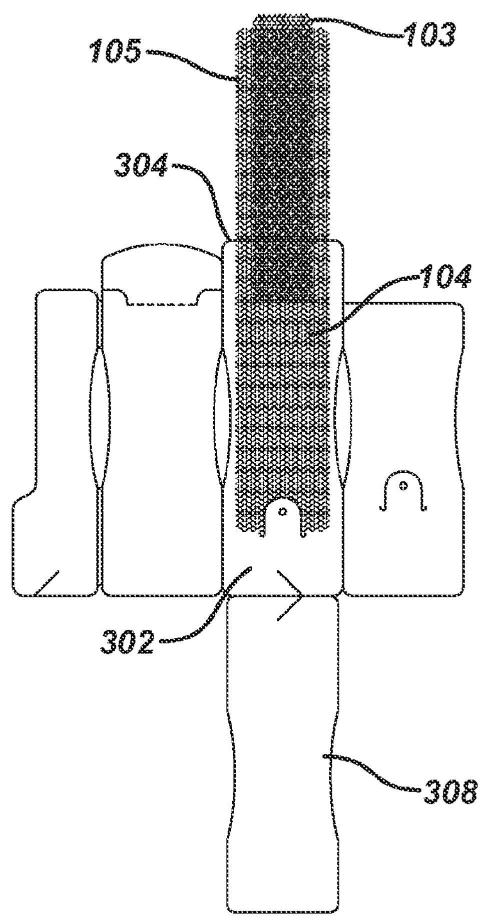
FIG. 4b
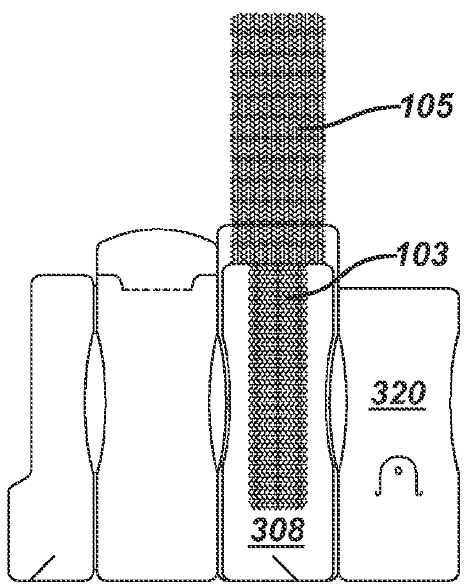
FIG. 4c
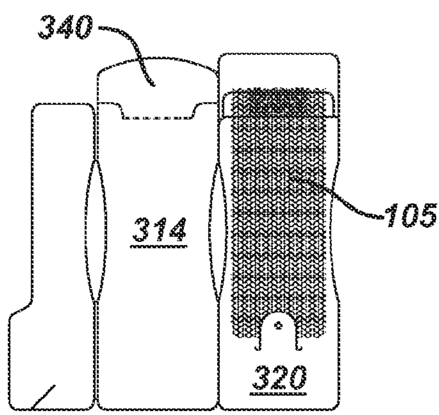
FIG. 4d

SURGICAL IMPLANT FOR TREATING PELVIC ORGAN PROLAPSE CONDITIONS

BACKGROUND OF THE INVENTION

1. Field of the Invention

The present invention relates generally to implants and methods for the treatment of pelvic organ prolapse conditions, and in particular for the treatment of vaginal prolapse conditions.

2. Background Discussion

Generally speaking, pelvic organ prolapse occurs when organs or structures within the pelvic cavity prolapse, or descend from their normal anatomical positions. These conditions can include the rectum descending into the back wall of the vagina to create a bulge that may affect bowel function (rectocele), herniation of the small bowel (enterocele), the uterus descending into the normal vaginal space (uterine prolapse), the bladder descending into the vagina typically as a result of a prolapse of the front wall of the vagina (cystocele), or even the vagina descending into the vaginal cavity itself (vaginal vault prolapse). Pelvic organ prolapse occurs as a result of weakening or damage to the muscles and tissues that support the vagina and surrounding organs that otherwise function to hold them in place, often due to the trauma of childbirth, loss of estrogen after menopause, or following a hysterectomy where removal of the uterus affects the normal structures holding the top of the vagina in place.

Various surgical treatments are available depending on the type and severity of the prolapse, most of which involve utilizing implantable meshes or other structures to help provide support to prolapsed organs, or various suspension techniques in which the surgeon attempts to reposition the prolapsed organ and secure or attach it to stronger, intact tissue in the pelvic cavity or to bone or periosteum.

For vaginal vault prolapse, the anatomical defect typically is in or around the upper portion of the vagina, and treatment involves reattachment of this portion of the vagina to stronger tissue or to the sacrum to thereby re-suspend the vagina in its normal anatomical position.

One known procedure for addressing vaginal vault prolapse utilizes a "Y-mesh" such as the ALYTE® Y-Mesh Graft sold by C.R. Bard, Inc. of Covington, Ga. The mesh includes first and second vaginal mesh flaps, and a sacral flap extending in the opposite direction from the vaginal mesh flaps. The two vaginal mesh flaps are positioned and secured on opposite surfaces, anterior and posterior, on the upper portion of the vagina. The vagina is then elevated into the proper position, and the sacral flap is attached to the sacral promontory, thereby suspending the vagina in its normal anatomical position.

The Y-mesh described above is comprised of the same mesh structure throughout, however the vaginal mesh flaps are extended with each end sewn together to form a single, double density sacral flap. Vaginal tissue to which the vaginal mesh flaps are secured, however, is very compliant tissue and ideally, the compliance of the mesh should mimic that of the natural tissue. The sacral flap should have a reasonable degree of stiffness in the longitudinal direction, as suspension of the vagina from the sacrum is via the sacral flap.

Although compliance of the vaginal flaps is important following implantation, it is also desirable that the implant have a reasonable degree of compliance prior to and during implantation to facilitate handling by the surgeon. Further, in known procedures, while the surgeon is attaching the first vaginal flap, the second vaginal flap is prone to interfere (both physical interference and visual obstruction), and typically requires the surgeon to temporarily restrain the second vaginal flap while securing the first vaginal flap.

An improved Y-mesh type implant having improved compliance properties and features would be highly desirable.

SUMMARY OF THE INVENTION

The present invention provides a surgical implant including a vaginal portion having a length, a width, a first end and a second end, and a central region positioned between the first and second ends, and a sacral portion having a length, a width, a first end and a second end, the first end of the sacral portion being coupled to the central region of the vaginal portion so that the width of the first end extends substantially perpendicularly to the length of the vaginal portion. The vaginal and sacral portions are made of the same substantially flat, planar mesh having substantially uniform properties throughout the implant and having an anisotropic knitted or woven structure that has a greater stiffness in a first direction than a second direction. The mesh of the sacral mesh portion is aligned such that the first direction is aligned in a longitudinal direction of the sacral portion and the mesh of the vaginal portion is aligned such that the stiffness in a longitudinal direction of the vaginal portion is less than that of the sacral portion.

According to one embodiment, the mesh is a partially absorbable mesh, that may further be made of a substantially equal mass of poliglecaprone-25 monofilament fibers and absorbable polypropylene monofilament fibers.

In another embodiment, the mesh of the vaginal portion is oriented in a first direction and the mesh of the sacral portion is oriented in a second direction that is substantially perpendicular to the first direction.

The surgical implant may further include an absorbable film coupled to at least the sacral portion of the mesh.

In alternate embodiments, the sacral portion is coupled to the vaginal portion by a sewn seam or by a laser weld.

In yet further alternate embodiments, the length and width of the sacral portion is approximately 14 cm and 3 cm respectively, and the length and width of the vaginal portion is approximately 13 cm and 5 cm respectively.

The vaginal portion may be made of a first vaginal flap extending from the central region to the first end, and a second vaginal flap extending from the central region to the second end, wherein at least one of the first and second vaginal flaps is biased to overlay the sacral portion when the implant is unconstrained.

Also provided is a surgical implant having a vaginal portion having a length, a width, a first end and a second end, and a central region positioned between the first and second ends. The vaginal portion is made of a mesh having a knit or weave pattern oriented in a first direction. The implant further includes a sacral portion having a length, a width, a first end and a second end, where the first end of the sacral portion is coupled to the central region of the vaginal portion so that the width of the first end extends substantially perpendicularly to the length of the vaginal portion. The sacral portion is comprised of the same mesh as the vaginal portion, and has a knit or weave pattern oriented in a second direction different than the first direction. In one embodiment, the second direction is substantially perpendicular to the first direction.

In another embodiment, the mesh is a partially absorbable mesh, which may be made of a substantially equal mass of poliglecaprone-25 monofilament fibers and absorbable polypropylene monofilament fibers.

The implant may further include an absorbable film coupled to at least the sacral portion of the mesh.

In yet another embodiment, the vaginal portion is made of a first vaginal flap extending from the central region to the first end, and a second vaginal flap extending from the central region to the second end, wherein at least one of the first and second vaginal flaps is biased to overlay the sacral portion when the implant is unconstrained.

Also provided is a surgical implant including a vaginal portion having a length, a width, a first end, a second end, and a central region positioned between the first and the second ends. The vaginal portion includes a first vaginal flap portion extending from the central region and terminating at said first end, and a second vaginal flap portion extending from the central region and terminating at said second end. The implant further includes a sacral portion having a length, a width, a first end and a second end, with the first end being coupled to the central region of the vaginal portion so that the first end of the sacral portion extends substantially perpendicularly to the length of the vaginal portion. At least the first vaginal flap is biased to substantially overlay the sacral portion when unconstrained. The implant may be made of a mesh, which may be partially absorbable and may further be made of a substantially equal mass of poliglecaprone-25 monofilament fibers and absorbable polypropylene monofilament fibers.

In yet another embodiment, at least one of the first and second vaginal flaps is biased to overlay the sacral portion when the implant is unconstrained.

BRIEF DESCRIPTION OF THE DRAWINGS

FIGS. 4*a*-4*d* illustrate various steps for assembling the package of FIG. 3 to hold the implant of FIG. 1;

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways.

Figure 1:
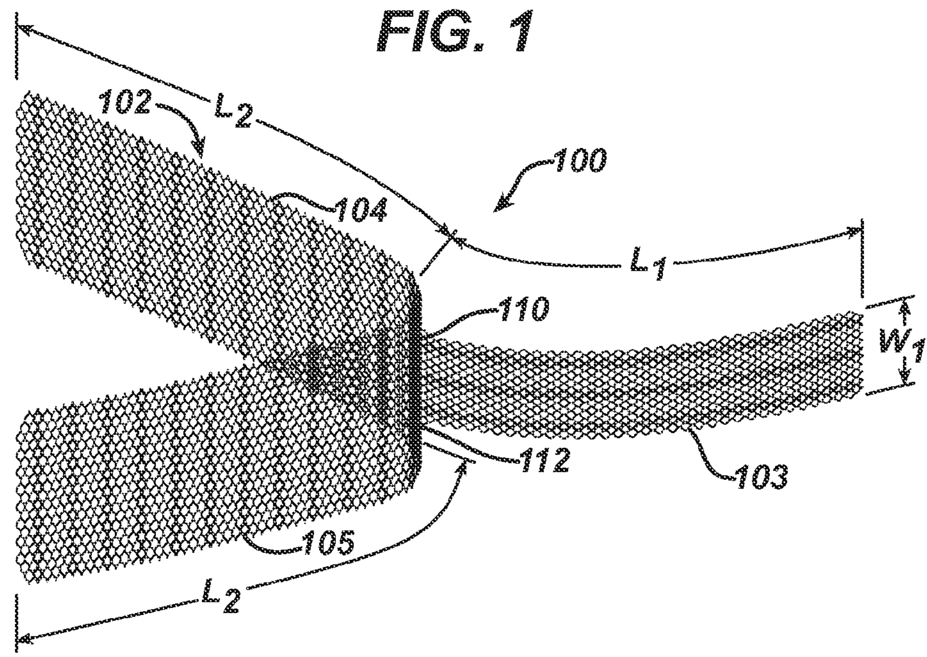
FIG. 1 is a perspective view of one embodiment of a surgical implant according to the present invention.
Figure 2:
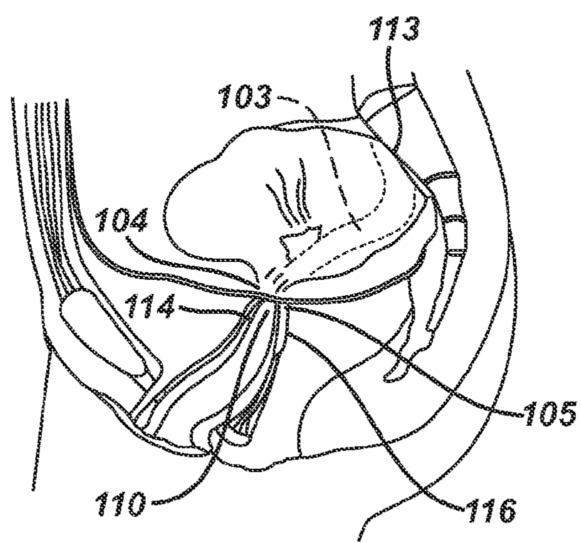
FIG. 2 is a side view illustrating the implant of FIG. 1 positioned within a patient.

One embodiment of a surgical implant 100 according to the present invention, and its use within a patient is illustrated in FIGS. 1 and 2. The implant 100 includes a vaginal portion 102 that is designed to be secured to vaginal tissue, and a sacral portion 103 that is secured to the sacrum 113 and operates to suspend the vaginal cuff 110 in the proper anatomical position. The vaginal portion is preferably made of a single continuous material that includes a first vaginal flap 104 and a second vaginal flap 105. The first vaginal flap 104 is attached to the anterior surface 114 of the vaginal wall and the second vaginal flap 105 is attached to the posterior surface 116 of the vaginal wall as illustrated in FIG. 2.

In one embodiment, the length $L_1$ and width $W_1$ of the sacral portion are approximately 14 cm and 3 cm respectively, and the length $L_2$ and width $W_2$ of each vaginal portion are approximately 13 cm and 5 cm respectively.

In a preferred embodiment, the entirety of the implant is comprised of the same, substantially flat, uniform mesh structure, which optimally is comprised of equal parts of absorbable poliglecaprone-25 monofilament fibers and non-absorbable polypropylene monofilament fibers. A mesh comprised of these materials and having a suitable knitting construction is commercially available as GYNEMESH M™ Partially Absorbable Mesh, and is manufactured and sold by Ethicon, Inc. of Somerville, N.J. As will be described further below, the partially absorbable nature of this mesh provides superior characteristics with regard to improved handling of the mesh in the surgical setting prior to hydrolysis of the absorbable components, and improved compliance following hydrolysis after it has been implanted, which is particularly important when secured to tissue such as highly compliant vaginal tissue. In one embodiment, selected polypropylene fibers may be dyed to help visually aid the surgeon during positioning, trimming and/or suturing of the implant. For example, longitudinal strands or strands extending laterally across the width may be dyed to indicate the direction of the mesh. Further, equal spacing of the strands may be used to indicate distances and/or sizes of the mesh.

The mesh material described above has a knitted construction that is anisotropic, meaning that because of the knit pattern, the mesh has different properties in one direction (i.e., longitudinally) than it does in a different direction. For implants of this type, it is desirable that the sacral flap have a greater stiffness in the longitudinal direction to enable it to have the necessary support to suspend the vagina from the sacrum. For the vaginal flaps, however, a lower stiffness is desirable to better approximate the compliant tissue properties of the vaginal tissue. According to one embodiment, although the same, uniform mesh material is used across the entire implant, the directional orientation of the mesh in the vaginal flaps is different from that in the sacral flap. The mesh of the sacral portion may be aligned so that its greatest stiffness is in the longitudinal direction, and the mesh of the vaginal portions may be aligned so as to have the least or simply less stiffness in the longitudinal direction. In one embodiment, the two are oriented substantially perpendicularly to one another. Further, additional temporary stiffening and also stress shielding of the mesh (keeping the mesh undistorted until the film degrades) may be achieved by applying an absorbable film, such as polydioxanone (PDO), to all or selected portions of the mesh.

Perpendicular alignment of the sacral and vaginal portions can be achieved by securing a first end 110 of a separate sacral flap to a substantially central region 112 of a separate vaginal portion. These components can be secured by any suitable manner, such as by a sewn seam, laser welding or the like. In a preferred embodiment, a seam is formed by sewing with polypropylene threads along the edge of the mesh and tied to the crossing with perpendicular threads, which resembles the mesh itself and largely retains the properties of the mesh in terms of elasticity in all directions, and the properties of the mesh in terms of mechanics and porosity.

As indicated previously, in a preferred embodiment, the mesh is comprised of the commercially available product GYNEMESH M™ Partially Absorbable Mesh. This mesh has an average pore size of 3.9 $mm^2$ before hydrolysis, and an average pore size of 4.6 $mm^2$ after hydrolysis (about 84 days). Known competitive meshes are comprised of all non-absorbable polypropylene and thus have a consistent pore size and amount of material that remains within the body. For example, the ALYTE® Y-Mesh Graft has a constant pore size of 2.01 $mm^2$ (sacral portion), and thus has a higher density of material remaining within the body. Further, the presently described implant has the following stiffness properties prior to and following hydrolysis:

| | Pre-Hydrolysis | Post-Hydrolysis |
|---|---|---|
| Bending Stiffness (Sacral Portion) | 454 mg-cm | 179 mg-cm |
| Bending Stiffness (Vaginal Portion) | 139 mg-cm | 18 mg-cm |

As a point of comparison, the ALYTE® Y-Mesh Graft has a sacral portion bending stiffness of 205 mg/cm and a vaginal portion bending stiffness of 86.1 mg/cm. Thus, the present device has far superior post-hydrolysis properties, particularly for the vaginal portion (18 mg/cm as compared to 86.1 mg/cm) which allows the implant to much better mimic the very compliant vaginal tissue. The sacral portion of the present device also has far superior bending stiffness prior to hydrolysis to aid in surgeon handling and initial suspension, and somewhat lower stiffness following hydrolysis for better compliance after implantation.

According to another aspect of the present invention, at least one, and preferably both, of the two vaginal flaps is formed to include a bend across its width such that the vaginal flap is biased to lay substantially over the sacral flap when unconstrained. This feature is highly advantageous in the surgical setting. In the known products described above, the vaginal flaps are biased to lay substantially over one another when unconstrained and with the sacral flap extending in the opposite direction. During surgical implantation, however, as the surgeon is attaching the first of the vaginal flap, the second vaginal flap physically and visually impairs the surgeon, and often requires that the second vaginal flap be tacked up out of the way, typically by temporarily suturing the second vaginal flap to the sacral flap. With a biased flap as described herein, the second vaginal flap remains out of the way, and does not require temporary fixation or the like.

Figure 5:
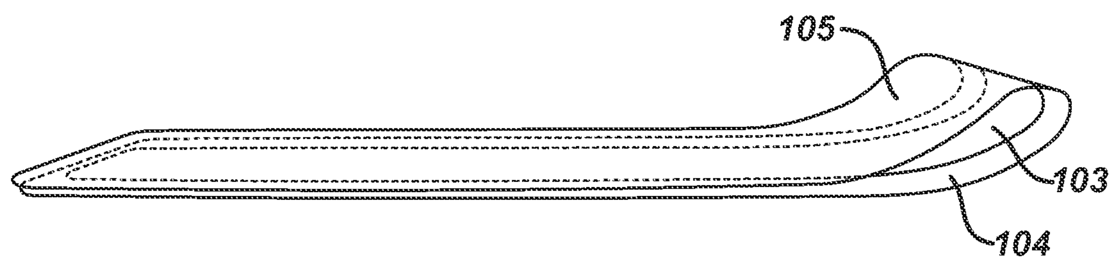
FIG. 5 illustrates the implant of FIG. 1 after packaging and sterilization according to another aspect of the present invention.

The biasing of the vaginal flap can be accomplished by pre-forming the mesh material, or more preferably is formed by specially designed packaging in combination with a sterilization process. An implant having the biased vaginal flaps resulting from packaging and sterilization is best shown in FIG. 5. Following fabrication and before packaging and sterilization, the implant lays substantially flat with the sacral portion 103 laying substantially flat over the first vaginal flap 104 and the second vaginal flap 105 laying substantially flat and extending in the opposite direction. Following packaging and sterilization, both vaginal flaps have a bend along their respective lengths and are biased to bend back over the sacral flap as shown in FIG. 5.

Figure 3:
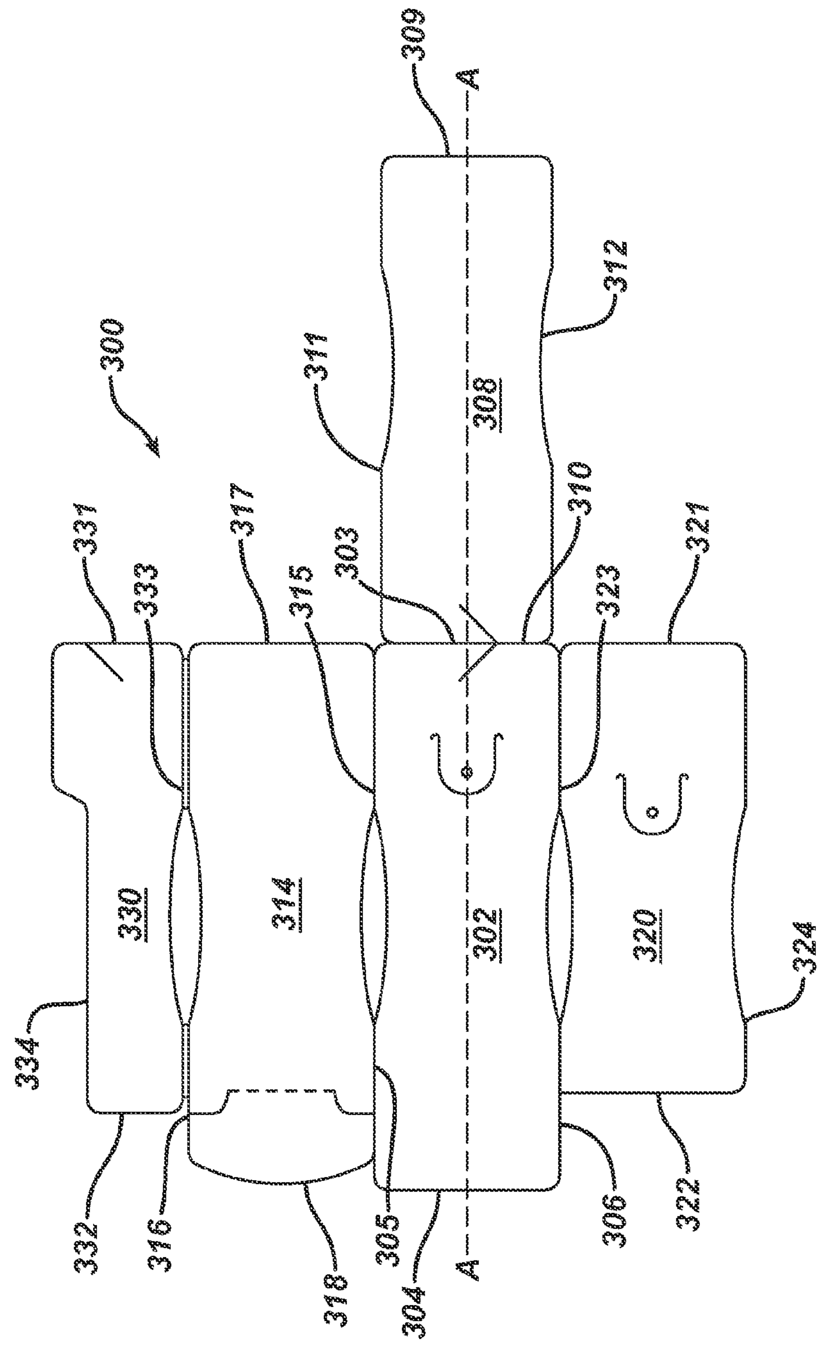
FIG. 3 is a plan view of an unassembled package suitable for use with the implant of FIG. 1.

One embodiment of a package that can be utilized to achieve biasing of the flaps as described above is illustrated in FIGS. 3 and 4*a*-4*f*. As best shown in FIG. 3, the package 300 includes a substantially flat, first center panel 302 extending along longitudinal axis A-A, a periphery of which is defined by first and second longitudinal edges 303, 304 and first and second lateral edges 305, 306. A substantially flat, second center panel 308 also extends along the longitudinal axis, and has a periphery defined by third and fourth longitudinal edges 309, 310 and third and fourth lateral edges 311, 312. At least a portion of the fourth longitudinal edge 310 is adjacent to and physically coupled with the first longitudinal edge 303 of the first center panel 302 as shown. The package further includes first and second lateral panels 314, 320 that extend longitudinally. The first lateral panel 314 is defined by fifth and sixth longitudinal edges 315, 316 and fifth and sixth lateral edges 317, 318. Similarly, the second lateral panel 320 is defined by seventh and eighth longitudinal edges 321, 322 and seventh and eighth lateral edges 323, 324. The first lateral panel is adjacent to and substantially aligned with the first center panel, and is coupled thereto along at least a portion of the respective fifth and first longitudinal edges. Similarly, the second lateral panel is adjacent to and substantially aligned with the first center panel, and is coupled thereto along at least a portion of the respective sixth and second longitudinal edges. The panels preferably are coupled to one another at a bendable seam or the like, so that the panels may movably be folded over one another at the seams. The package further includes a third lateral panel 330 also extending in the longitudinal direction but positioned lateral of the first lateral panel. The third lateral panel is defined by ninth and tenth longitudinal edges 331, 332 and ninth and tenth lateral edges 333, 334. The ninth lateral edge 331 is substantially aligned with and coupled to, along at least part of its length, the sixth lateral edge 315 of the first center panel.

The manner in which the package 300 is assembled and holds the implant of the present invention is best illustrated by FIGS. 4*a*-4*f*. The implant 100 is positioned so that the first vaginal flap 104 is positioned substantially on top of the first center panel 302 and the second vaginal flap 105 and sacral flap 103 extend outwardly from the second longitudinal edge 304 and exterior to the package.

Figure 4E:
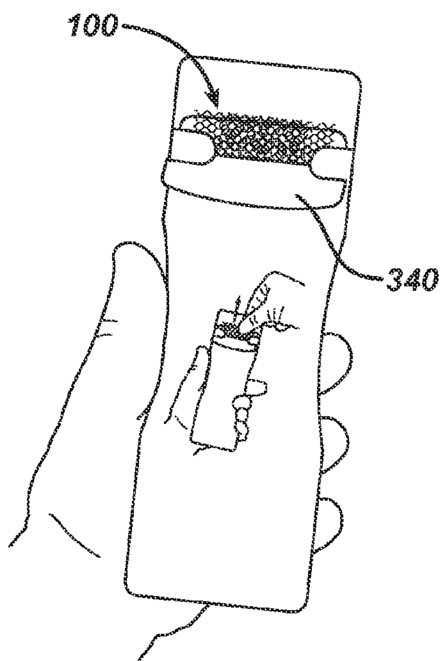
FIGS. 4*e*-4*f* illustrate the combination implant and package fully assembled.
Figure 4F:
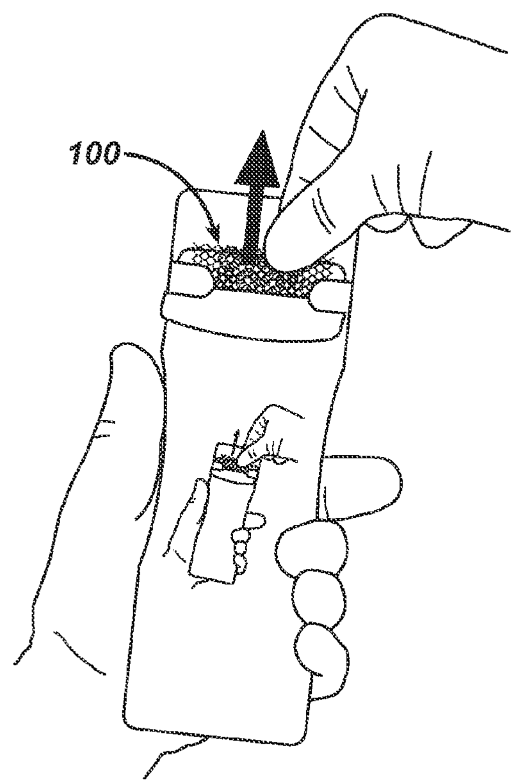

The second center panel 308 is then folded over the first center panel 302, and the sacral portion 103 positioned over the second center panel as shown in FIG. 4*b*. Subsequently, the second lateral panel 320 is folded over the sacral portion, and the second vaginal flap 105 is positioned substantially over the second lateral panel as shown in FIG. 4*c*. The first lateral panel 314 is then folded over the second vaginal flap 105 and the third lateral panel 330 folded over to complete the package as shown in FIG. 4*d*. The second lateral panel 314 may further include a foldable end portion 340 that, once the package is assembled, can be folded down to reveal the implant as shown in FIG. 4*e*, such that the user can grasp the implant to remove it from the package as shown in FIG. 4*f* with one hand and in one step, without any further unfolding or disassembly of the package.

As described above, the implant is packaged so that the three mesh flaps are aligned substantially on top of one another, but are each separated by a panel of the package. In this manner one of the three flaps lies in an unconstrained position, while two of the three flaps that are folded back over the first one are held in a biased or constrained position. Once the package and implant are assembled, the entire assembly is sterilized by any suitable manner such as ethylene oxide. The sterilization process causes the biased mesh flaps to take on a "heat set", such that once dispensed from the package these flaps are now biased toward the packaged position, which results in at least one of the vaginal flaps to remain biased to fold over the sacral flap. As indicated previously, this is advantageous during surgical implantation, as it overcomes the previously known problem of having the second vaginal flap physically and visually obstructing the surgeon while securing the first vaginal flap, and avoids the need to temporarily suture or tack the second vaginal flap out of the way.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A surgical implant comprising:

a vaginal portion having a length, a width, a first end, a second end, and a central region positioned between the first and the second ends, the vaginal portion including a first vaginal flap portion extending from the central region and terminating at said first end, and a second vaginal flap portion extending from the central region and terminating at said second end;

a sacral portion having a length, a width, a first end and a second end, the first end of the sacral portion being coupled to the central region of the vaginal portion so that the first end of the sacral portion extends substantially perpendicularly to the length of the vaginal portion;

wherein at least the first vaginal flap is heat set along its length so as to be biased to substantially overlay the sacral portion when unconstrained.

2. The surgical implant according to claim 1, wherein the implant is comprised of a mesh.

3. The surgical implant according to claim 2, wherein the mesh is partially absorbable.

4. The surgical implant according to claim 3, wherein the mesh is comprised of a substantially equal mass of poliglecaprone-25 monofilament fibers and absorbable polypropylene monofilament fibers.

5. The surgical implant according to claim 2, wherein the length and width of the sacral portion is approximately 14 cm and 3 cm respectively.

6. The surgical implant according to claim 5, wherein the length and width of the vaginal portion is approximately 13 cm and 5 cm respectively.

7. The surgical implant according to claim 1, wherein at least one of the first and second vaginal flaps is biased to overlay the sacral portion when the implant is unconstrained.

* * * * *